United States Patent [19]
Naegeli et al.
[11] Patent Number: 4,496,476
[45] Date of Patent: Jan. 29, 1985

[54] ODORANTS CONTAINING CIS-3,7-DIMETHYLOCTA-3,6-DIENOIC ACID

[75] Inventors: Peter Naegeli, Wettingen, Switzerland; Martin Rohr, Glen Rock, N.J.

[73] Assignee: Givaudan Corporation, Clifton, N.J.

[21] Appl. No.: 410,296

[22] Filed: Aug. 23, 1982

[30] Foreign Application Priority Data

Sep. 9, 1981 [CH] Switzerland ........................ 5823/81

[51] Int. Cl.[3] ................................................ A61K 7/46

[52] U.S. Cl. ................................ 252/522 R; 426/534; 131/276

[58] Field of Search .................................... 252/522 R

[56] References Cited

U.S. PATENT DOCUMENTS 3,553,110 1/1971 Mitchell et al. ................ 252/522 R

OTHER PUBLICATIONS

Arctander, "Perfume & Flavor Chemicals," 1969, vol. I, No. 1451.

J. J. Hurst et al., J. Chem. Soc., (1960), 2864–2869.

W. F. Erman, J. Amer. Chem. Soc., 89, (1967), 3828–3841.

W. F. Erman et al., J. Org. Chem., 34, (1968), 2196–2203.

*Primary Examiner*—Anton H. Sutto
*Attorney, Agent, or Firm*—Robert F. Tavares

[57] ABSTRACT

This invention concerns the use of cis-3,7-dimethylocta-3,6-dienoic acid as an odorant and/or flavorant, odorant and flavorant compositions containing same and methods for preparing same. This invention also concerns such compositions and methods wherein the cis-3,7-dimethylocta-3,6-dienoic acid is used in combination with 2,2,4-trimethylcyclohex-3(or 4)-ene-carboxylic acid.

6 Claims, No Drawings

ODORANTS CONTAINING CIS-3,7-DIMETHYLOCTA-3,6-DIENOIC ACID

THE INVENTION

This invention concerns the use of cis-3,7-dimethylocta-3,6-dienoic acid as an odorant and/or a flavorant, the novel odorant and/or flavorant compositions containing the named compound and methods for preparing such compositions. The cis-3,7-dimethylocta-3,6-dienoic acid (also known as cis-isogeranic acid) is a known compound, [see J. Chem. Soc., 2864 (1960) and J. Am. Chem. Soc., 89, 3828 (1960)] and can be represented by the structure

I

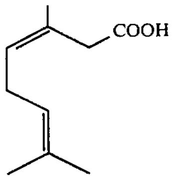

The prior art does not disclose any organoleptic properties nor any utility for this compound other than as a chemical intermediate.

Surprisingly and unexpectedly, this acid has an extremely strong smelling and tremendously tenaceous odor which is described as metallic, resinous, and strongly reminiscent of the odor which is observed upon entering old churches. These unique odor properties make the cis-3,7-dimethylocta-3,6-dienoic acid particularly valuable in the formulation of odorants. The compound has also been found to be exceptionally suitable as a flavorant for food products and tobacco.

It is a further aspect of this invention that the compound of formula I can be combined harmoniously with 2,2,4-trimethylcyclohex-3(or 4)-ene-carboxylic acid as will be further described below.

DESCRIPTION OF THE PREFERRED EMBODIMENTS

The cis-3,7-dimethylocta-3,6-dienoic acid of formula I has an extremely strong smell and tremendously tenacious odor which can be described as metallic, resinous and strongly reminiscent of the odor which is observed upon entering old churches. These olfactory properties are completely different from the related trans-isogeranic acid (see formula I') or the geranic acids of formula I''

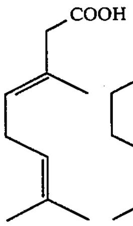

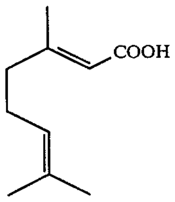

or

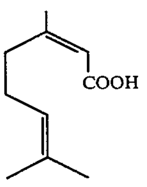

I'

I'' trans-isogeranic acid geranic acids

In contrast to the compound used in this invention, the trans-isogeranic acid has an odor which is described as weak smelling, slightly burning, acid-like and perfumistically uninteresting. The geranic acids I'' can be described as mild, green-flowery, slightly herbaceous, fresh, and with woody undertones.

Threshold value determinations have revealed that the compound of formula I is almost ten to the power of two more intensive than the compound of formula I' or the compounds of formula I''. The compound of formula I is therefore a typical "impact chemical".

In the course of the investigation it was further discovered that the acid of formula I combines harmoniously with 2,2,4-trimethylcyclohex-3(or 4)-ene-carboxylic acid which can be represented by the formula

II

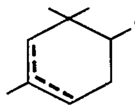

This compound has been described in the literature; see J. Org. Chem. 34, 2196 (1968) and J. Am. Chem. Soc. 89, 3828 (1967). Although the individual isomers of the compound of formula II are readily accessible, it is convenient to use the isomer mixture.

The olfactory properties of the trimethylcyclohexenoic acid of formula II can be described as very natural, bottom notes of frankincense, olibanum, cistus, amber-like, leather-like, myrrh, animal-like, opoponax and antique wood. The combination of the cis-isogeranic acid of formula I and the acid of formula II exhibits surprising organoleptic properties. The compound of formula II does not compete with the much more intense cis-isogeranic acid, but tends to blend with it in a beneficial way so as to strengthen its natural notes, provide rounding-off effects and underline its resinous notes. Based on their natural odor notes, the compound of formula I or a mixture of the compound of formula I and the compound of formula II is particularly suitable for modifying known compositions.

The compounds of formulas I and II combine with numerous known odorant ingredients of natural or synthetic origin. The range of the natural, raw substances can embrace not only readily-volatile but also semi-volatile and less volatile components and the range of the synthetic ingredients can embrace representatives from practically all classes of substances, as will be evident from the following compilation:

- Natural products such as basil oil, tree moss absolute, benzoin balsam, bergamot oil, castoreum, cedarwood oil, cistus oils, lemon oil, coriander oil, cypress oil, elemi oil, pine needle oil, galbanum oil, grapefruit oil, jasmine absolute, lavender oil, mandarin oil, mastix absolute, musk oils, myrtle oil, palmarosa oil, patchouli oil, petitgrain oil Paraguay, peppermint oils, pepper oil, rosemary oil, sandalwood oil, terpentine oils, thyme oil, vetiver oil, wormwood oil, ylang oil, civet extracts etc.
- Alcohols such as citronellol, geraniol, linalool, nerol, phenylethyl alcohol, rhodinol, Sandalore® [3-methyl-5-(2,2,3-trimethylcyclopent-3-en-1-yl)-pentan-2-ol], Sandela® [3-isocamphyl-(5)-cyclohexanol], cinnamic alcohol etc.
- Aldehydes such as anisaldehyde, benzaldehyde, citral, helional (α-methyl 3,4-methylenedioxyhydrocinnamaldehyde), heliotropin, α-hexylcinnamaldehyde, hydroxycitronellal, lauric aldehyde, Lilial® (p-tert-butyl-α-methylhydrocinnamaldehyde), methylnonylacetaldehyde, undecylene aldehyde, vanillin, cinnamaldehyde etc.

Ketones such as acetophenones (e.g. p-methyl,p-methoxy), acetylcedrene, allyl ionone, irones, α-ionone, β-ionone, musk ketone, methyl ionone etc.

Esters such as ethyl acetoacetate, allyl phenoxyacetate, anthranilic acid esters, benzyl acetate, cinnamyl propionate, dimethylbenzycarbinyl butyrate, fatty acid esters, linalyl acetate, Metambrate TM (1-acetoxy-1-methyl-2-sec-butylcyclohexane), methyl dihydrojasmonate, salicylates, styrallyl acetate, vetiveryl acetate etc.

Lactones such as ethylene brassylate, coumarin, γ-nonalactone, γ-undecalactone, $C_{14}$-aldehyde (δ-undecalactone) etc.

Ethers such as caryophyllene epoxide, cyclododecanol ethers such as Madrox TM (1-methyl-1-methoxy-cyclododecane), epoxycedrene etc.

Various components often used in perfumery such as musk ambrette, Crysolide® (4-acetyl-6-tert-butyl-1,1-dimethylindane), eugenol, Galaxolid® (1,3,4,6,7,8-hexahydro-4,6,6,7,8,8-hexamethyl-cyclopenta-γ-2-benzopyran), indole, isobutylquinoline, p-menthane-8-thiol-3-one, methyleugenol, Musk 174 TM (12-oxa-hexadecanolide) etc.

The cis-isogeranic acid of formula I, or a mixture of I and II, rounds-off and harmonizes in an impressive and remarkable manner the odor notes of known compositions, for example, oriental (i.e. heavy, sweet) notes, amber notes, powdery notes, citrus notes in colognes and the like. For example, in perfume bases (e.g. in rose bases) it underlines the desired character of the heavy, sweet and somewhat fruity acting Bulgarian rose.

In fruit bases (e.g. of the apricot type) the compound of formula I, or a mixture of I and II can be used successively to produce a more powerful and more natural-fruity effect as well as a rounded-off effect.

The compound of formula I, or a mixture of I and II, can be used in wide limits, which can extend in compositions from 0.01% (detergents) to 10% (alcoholic solutions). It should be appreciated however, that these amounts are not limiting since the experienced perfumer can also achieve effects with lower concentrations or can synthesize novel complexes with higher amounts. The preferred concentrations vary between 0.1% and 5%.

The compositions produced with the compound of formula I can be used for all kinds of perfumed consumer goods (eau de cologne, eau de toilette, essences, lotions, creams, shampoos, soaps, salves, powders, toothpastes, mouth washes, deodorants, detergents, tobacco etc.).

The compound of formula I, or a mixture of I and II, can be used in the production of odorant compositions and, as will be evident from the foregoing compilation, can be used with a wide range of known odorants or mixtures of odorants. In the production of such compositions, the known odorants or mixtures of odorants specified earlier can be used according to methods known to the perfumer; see W. A. Poucher, Perfumes, Cosmetics, Soaps 2, 7th Edition, Chapman and Hall, London 1974.

The compound of formula I or its mixture with the compound of formula II is also excellently suited for use in flavors, especially in fruit flavors of various kinds. It is especially useful for the flavoring of tobacco.

As a flavorant the compound of formula I can be used, for improving, intensifying, enhancing or modifying fruit flavors of various kinds (e.g. raspberry or apricot flavors). These flavors can be used in foodstuffs (yoghurt, confectionery etc.), luxury consumables (tea, tobacco etc.) and drinks (lemonade etc.).

The pronounced flavor qualities of the compound of formula I (or a mixture of I and II) enable it to be used as a flavorant in low concentrations. A suitable range is, for example, 0.01 ppm–100 ppm, preferably 0.1 ppm–20 ppm, in the finished product (i.e. the flavored foodstuff, luxury consumable or drink).

In the flavoring of tobacco, the range in the case of a top flavor can be, for example from about 0.1 ppm to 2 ppm in the end product.

The named compounds can be mixed with other ingredients used for flavoring compositions or can be added to such flavorants in the customary manner. Among the flavorants contemplated in accordance with the invention there are to be understood flavoring compositions which can be diluted or dispersed in edible materials in a manner known per se. They contain, for example, about 0.1–10 weight %, especially 0.5–3 weight % of the compounds. They can be converted, according to methods known per se, into the usual forms of use such as solutions, pastes or powders. The products can be spray-dried, vacuum-dried or lyophilized.

The known flavorants conveniently used in the production of such flavoring compositions are either referred to in the foregoing compilation or can be taken from the respective literature (see for example, J. Merory, Food Flavorings, Composition, Manufacture and Use, Second Edition, The Avi Publishing Company, Inc., Westport, Conn. 1968, or G. Fenaroli, Fenaroli's Handbook of Flavour Ingredients, Second Edition, Volume 2, CRC Press, Inc. Cleveland, Ohio 1975).

For the production of the usual forms of use there can be used, for example, the following carrier materials, thickening agents, flavor-improvers, spices, auxiliary ingredients. etc:

Gum arabic, tragacanth, salts or brewer's yeast, alginates, carrageen or similar absorbents; indoles, maltol, dienals, spice oleoresins, smoke flavors; cloves, diacetyl, sodium citrate; monosodium glutamate, disodium inosine-5'-monophosphate (IMP), disodium guanosine-5-phosphate (GMP); or special flavoring substances, water, ethanol, propyleneglycol, glycerine.

The compound of formula I (or a mixture of I and II) can be used, in particular, for improving the organoleptic properties of tobacco products.

The term "tobacco product" is a general term commonly used in the trade and includes not only tobacco itself but also tobacco by-products such as reconstituted and homogenized leaf and stem, tobacco surrogate (e.g. lettuce and cabbage leaf etc.), materials which are used in tobacco processing such as paper, filters etc. and flavoring substance compositions used for tobacco products. Cigarette tobacco, cigar tobacco, chewing tobacco, pipe tobacco etc. fall under the term "tobacco product".

The addition of the compound of formula I, or a mixture of I and II, to a tobacco mixture improves not only the odor of fresh tobacco but also the odor and the flavor of the tobacco when smoked. A comparison of treated with untreated tobacco shows that the odor of the mixtures containing the compound of formula I vis-à-vis the untreated tobacco is strengthened, more rounded-off and lighter.

The differences between the treated and untreated tobaccos are still more conspicuous when smoked. The untreated cigarettes exhibit, when smoked, an undesirable harshness, an effect which is reduced by adding the compound of formula I, or a mixture of I and II. When smoked, the treated cigarettes give a softer, lighter and more rounded-off flavor and are thus clearly preferred to the untreated cigarettes.

The amount of the compound of formula I, or of a mixture of I and II, which is conveniently added can depend on various factors, including the desired effect, the kind and the amount of other simultaneously used additives and/or the personal preference of the flavorist. Amounts as little as 0.01 ppm, based on the weight of the tobacco, have been found to be effective, while, however, amounts as high as 10 ppm can also be used. Amounts of 0.1 ppm to 2 ppm are, however, preferred.

It will be appreciated that the limits proposed earlier are intended to indicate only the preferred amounts; these are, however, dependent on the skill of the flavorist and the effect which he wishes to produce.

The compounds of formulas I and II can be added to or mixed with the tobacco product (cigarette paper, etc.) according to methods known to the person skilled in the art (e.g. by spraying, immersion, coating etc.).

ILLUSTRATION OF THE PREFERRED EMBODIMENTS

The following examples illustrate the preferred embodiments of the present invention, and should not be construed as limiting. They are also intended to embrace variations derivable therefrom, which are obvious to the person skilled in the art.

With regard to the ratio of compound of formula I to compound of formula II, this can vary within wide limits. A suitable range is, for example, 90:1 to 1:90.

EXAMPLES

1. Flowery perfumery base.

| | Parts by weight |
|---|---|
| Hydroxycitronellal | 250 |
| Vetivenyl acetate | 100 |
| Bergamot oil | 100 |
| Sandela ® (Givaudan) | 100 |
| Phenylethyl alcohol | 60 |
| Isoraldein | 60 |
| Jasmine (synthetic) | 50 |
| Rhodinol (natural) | 50 |
| Musk ketone | 30 |
| Ylang (synthetic) | 20 |
| C—12-aldehyde (lauric) [10% in dipropylene glycol (DPG)] | 20 |
| Coumarin | 20 |
| Undecylene aldehyde (10% in DPG) | 10 |
| Dipropylene glycol | 125 |
| | 995 |

If 5 parts of the compound of formula I are added to this flowery composition, then the latter becomes much rounder and warmer. The lactone note (jasmine note) is very pleasantly underlined.

2. Fruity perfumery complex.

| | Parts by weight |
|---|---|
| Bergamot oil | 200 |
| Grapefruit oil | 200 |
| Corps Cassia ® (Givaudan) | 200 |
| $\beta$-Ionone | 200 |

-continued

2. Fruity perfumery complex.

| | Parts by weight |
|---|---|
| Vanillin | 190 |
| | 990 |

If 10 parts of the compound of formula I are added to this complex, then in the 24 hour dryout it becomes immediately recognizable that the compound of formula I fits in very harmoniously and can eclipse the somewhat sharp impression of the original base. Freshly dipped, the grapefruit note now appears underlined. On the other hand, the same amount of geranic acids would throw an undesirable eau de cologne note into bold relief in this composition.

3. Perfumery composition in the direction of fougere.

| | Parts by weight |
|---|---|
| Lavender oil | 210 |
| Amyl salicylate | 200 |
| Tree moss (50% in dipropylene glycol) | 100 |
| Citronellol | 100 |
| Geraniol | 80 |
| Musk ambrette | 80 |
| Bergamot oil | 80 |
| $\alpha$-Ionone | 80 |
| $\alpha$-Amylcinnamaldehyde | 25 |
| Eugenol | 20 |
| Metambrate TM (Givaudan) | 23 |
| | 998 |

By adding 2 parts of the compound of formula I the fresh effect of the base in increased substantially. In contrast thereto, geranic acids do not fit into the base at all.

4. Perfumery base of the "Carbochard" (chypre) type.

| | Parts by weight |
|---|---|
| Isoraldein | 200 |
| Musk ambrette | 100 |
| Phenylethyl alcohol | 100 |
| Bergamot oil | 100 |
| Tree moss | 50 |
| Vetivenyl acetate | 50 |
| Jasmine (synthetic) | 50 |
| Patchouli oil | 40 |
| Rhodinol (natural) | 40 |
| Eugenol | 40 |
| Sandala ® (Givaudan) | 40 |
| $\alpha$-Hexylcinnamaldehyde | 40 |
| Madrox TM (Givaudan) | 30 |
| Civet (synthetic) [10% in dipropylene glycol (DPG)] | 20 |
| Styrallyl acetate | 20 |
| Castoreum (synthetic) | 2 |
| Isobutylquinoline (10% in DPG) | 10 |
| Hydroxycitronellal | 45 |
| Undecylene aldehyde (10% in DPG) | 10 |
| Lemon oil | 5 |
| Undecalactone | 2 |
| Labdanum resinoid | 1 |
| | 995 |

By adding 5 parts of the compound of formula I the soft ionone note of the base is pleasantly emphasized in the 48 hours dryout. On the other hand, an addition of geranic acids emphasizes the cedar-like note too strongly and the resulting base becomes too dry.

| 5. Perfumery base of the chypre type. | Parts by weight |
|---|---|
| Madrox TM (Givaudan) | 200 |
| Bergamot oil | 150 |
| Hydroxycitronellal | 100 |
| Citronellol | 80 |
| Petitgrain oil | 60 |
| Musk 174 TM (Naarden) | 60 |
| Coriander oil | 40 |
| Galbanum oil | 40 |
| Cedarwood oil | 40 |
| Patchouli oil | 40 |
| Lemon oil | 40 |
| Elemi oil | 10 |
| Oak moss | 25 |
| Pine oil (Pumillon) | 110 |
| | 995 |

If 5 parts of a 10% solution of the compound of formula I are added to this chypre base, then the base becomes much more diffusive and sweeter. In the 24 hour dryout (bottom) an advantageous vetiver-citrus note is established. On the other hand, an equivalent addition of geranic acids to the composition gives rise to the appearance of unpleasant, dusty and musty notes.

| 6. Perfumery base in the direction of gardenia. | Parts by weight |
|---|---|
| Hydroxycitronellal | 150 |
| Bergamot oil | 140 |
| α-Ionone | 100 |
| α-Amylcinnamaldehyde | 85 |
| Heliotropin | 80 |
| Styrallyl acetate | 80 |
| Ylang oil | 80 |
| Benzyl acetate | 80 |
| Phenylethyl alcohol | 80 |
| Linalool | 80 |
| Nonalactone (10% in dipropylene glycol) | 20 |
| Jasmine (synthetic) | 15 |
| Undecalactone (10% in dipropylene glycol) | 7 |
| | 997 |

If 3 parts of the compound of formula I are added to this gardenia base, then the base is rounded-off in a very pleasant manner. On the other hand, by adding 3 parts of geranic acids the base is influenced in a negative manner; it does not become rounded-off at all.

| 7. Animal-like base. | Parts by weight |
|---|---|
| Sandela ® (Givaudan) | 100 |
| Madrox TM (Givaudan) | 100 |
| Acetylcedrene | 100 |
| Patchouli oil | 50 |
| Benzyl salicylate | 40 |
| Linalyl acetate | 40 |
| Myrrh oil | 30 |
| Benzoin resinoil (Siamese) | 30 |
| Ethylene brassylate | 30 |
| Castoreum (synthetic) | 30 |
| C—11-aldehyde (10% in DPG) | 20 |
| C—12-aldehyde (10% in DPG) | 20 |
| β-Ionone | 20 |
| p-Cresyl-phenyl acetate | 5 |
| Indole | 5 |
| DPG | ad 1000 |

If 10 parts of cis-isogeranic acid are added to the foregoing base, then the animal-like note becomes still more pronounced. This effect can not be produced with the same additions of geranic acids. The latter acids make the base unbalanced flowery, the aldehyde note standing out. Not only after 24, 48, 72 but also after 96 hours, the bottom note in the first case is warmest, most voluminous and most animal-like of the typical kind on the smelling strips.

| 8. Chypre perfumery base. | Parts by weight |
|---|---|
| Styrallyl acetate | 20 |
| Methylnonylacetaldehyde (10% in DPG) | 20 |
| Vetiveryl acetate | 50 |
| Rhodinol | 50 |
| Patchouli oil | 50 |
| Tree moss absolute (5% in DPG) | 50 |
| p-Tert.butyl-α-methylhydrocinnamaldehyde | 100 |
| Hydroxycitronellal | 100 |
| Methyl ionone | 100 |
| Musk ambrette | 100 |
| Coumarin | 100 |
| Bergamot oil | 100 |
| Dipropylene glycol | ad 1000 |

An addition of 10 parts of cis-isogeranic acid to the foregoing base intensifies (in contrast to geranic acids) the citrus character tremendously, the woody note being simultaneously intensified. It carries this citrus character harmoniously into the bottom in which, after 24 hours, a fine, warm moist-acid like nuance manifests itself and persists on the smelling strips over 96 hours. On the other hand, addition of the geranic acids damages the harmony of the composition.

| 9. Perfumery base in the direction of wood. | Parts by weight |
|---|---|
| Madrox TM (Givaudan) | 150 |
| Vetivenyl acetate | 150 |
| Sandela ® (Givaudan) | 150 |
| Linalool | 100 |
| Patchouli oil | 50 |
| Ironal ® (Givaudan) (α-irone) | 50 |
| Linalyl acetate | 50 |
| Citronellol | 50 |
| Benzyl acetate | 30 |
| Tree moss (colourless, absolute) | 30 |
| α-Amylcinnamaldehyde | 20 |
| Methylnonylacetaldehyde (10% in DPG) | 20 |
| Eugenol | 20 |
| C—11-aldehyde (10% in DPG) | 10 |
| Ciste oil (French) | 10 |
| Sandalore ® (Givaudan) | 10 |
| DPG | ad 1000 |

An addition of 10 parts of cis-isogeranic acid to the foregoing base brings about a clearer, more powerful woody note which is detected on the smelling strips even after 48, 72 and 96 hours. The geranic acids do not produce this effect.

| 10. Spicy base. | Parts by weight |
|---|---|
| Benzyl acetate | 100 |
| Hydroxycitronellal | 100 |
| Phenylethyl alcohol | 100 |
| Amyl salicylate | 100 |
| Patchouli oil | 80 |
| Ylang oil | 50 |
| Eugenol | 50 |
| Linalyl acetate | 60 |
| Musk ketone | 50 |
| Cedryl acetate | 30 |
| Epoxycedrene | 30 |

-continued

| 10. Spicy base. | Parts by weight |
|---|---|
| Acetylcedrene | 30 |
| Coumarin | 30 |
| Spearmint oil | 15 |
| Thyme oil | 15 |
| Methyl salicylate | 5 |
| Lemon oil | 5 |
| DPG | ad 1000 |

If 10 parts of cis-isogeranic acid are added to the foregoing base, then the composition becomes more powerful on the freshly dipped smelling strips and above all more balanced than with the addition of the same amount of geranic acids. This power and harmony still remains in the bottom note after 24, 48 and 96 hours.

| 11. Perfumery base (woody, forest-like) containing a mixture of 30 parts of the compound of formula I and 70 parts of the compound of formula II. | Parts by weight |
|---|---|
| Turpentine oil (rectified) | 200 |
| Elemi oil | 100 |
| Cypress oil | 100 |
| Bornyl acetate | 50 |
| Cedryl acetate | 50 |
| Myrrh oil | 10 |
| Tree moss (colourless) | 10 |
| Acetylcedrene | 10 |
| Caryophyllene | 5 |
| Ciste labdanum oil (10% in DPG) | 5 |
| Dipropylene glycol | 450 |
| | 990 |

By adding 10 g of the foregoing mixture the original base (woody, forest-like) is altered characteristically in the direction of frankincense (olibanum, incense, frankincense), is intensified immensely and, moreover, is much more resinous. Even after 72 hours the composition is still much more powerful in the bottom; the frankincense character remains completely.

12. A tobacco flavour (so-called top flavour in the direction of apricot) can be made up as follows:

| | Parts by weight | |
|---|---|---|
| | A | B |
| Terpenyl acetate | 0.25 | 0.25 |
| Methyl anthranilate | 0.25 | 0.25 |
| Linalyl acetate | 0.3 | 0.3 |
| Nerol | 0.5 | 0.5 |
| Cinnamaldehyde | 0.5 | 0.5 |
| Geraniol | 1.5 | 1.5 |
| Petitgrain oil (Paraguay) | 2.5 | 2.5 |
| Amyl butyrate | 10.0 | 10.0 |
| Isoamyl acetate | 10.0 | 10.0 |
| Isoamyl isovalerate | 15.0 | 15.0 |
| Amyl formate | 20.0 | 20.0 |
| Ethyl caproate | 20.0 | 20.0 |
| α-Ionone | 30.0 | 30.0 |
| Ethyl oenanthate | 30.0 | 30.0 |
| Ethyl isovalerate | 45.0 | 45.0 |
| Vanillin | 85.0 | 85.0 |
| Benzaldehyde | 120.0 | 120.0 |
| $C_{14}$—aldehyde(γ-undecalactone) | 125.0 | 125.0 |
| Ethyl alcohol | 484.2 | 464.2 |
| Compound of formula I | — | 20.0 |
| | 1,000.0 | 1,000.0 |

By adding the compound of formula I to composition A the fruity note present is clearly intensified. When the flavoured tobacco is smoked a substantially more pronounced fruity note is ascertainable and, in addition, the tobacco note is also clearly intensified.

We claim:

1. A fragrance composition comprising an olfactorily effective amount of cis-3,7-dimethylocta-3,6-dienoic acid and at least one other olfactory agent.

2. A fragrance composition comprising an olfactorily effective amount of a mixture of cis-3,7-dimethylocta-3,6-dienoic acid and 2,2,4-trimethylcyclohex-3(or 4)-ene-carboxylic acid and at least one other olfactory agent.

3. A fragrance composition according to claims 1 or 2 wherein the fragrance composition is of the floral, fruity, fougère, chypre, animalic, woody or spicy type.

4. A method for improving the odor of a fragrance composition which comprises adding thereto an olfactorily effective amount of cis-3,7-dimethyl-3,6-dienoic acid.

5. A method for improving the odor of a fragrance composition which comprises adding thereto an olfactorily effective amount of a mixture of cis-3,7-dimethylocta-3,6-dienoic acid and 2,2,4-trimethylcyclohex-3(or 4)-ene-carboxylic acid.

6. The method of claim 4 or 5 wherein the fragrance composition to be improved is selected from floral, fruity, fougère, chypre, animalic, woody, spicy.

* * * * *